United States Patent [19]

Chen et al.

[11] Patent Number: 5,635,239

[45] Date of Patent: Jun. 3, 1997

[54] ABSORBENT STRUCTURE POSSESSING IMPROVED INTEGRITY

[75] Inventors: Franklin M. C. Chen; David L. LeMahieu, both of Appleton; William S. Pomplun; Dave A. Soerens, both of Neenah, all of Wis.

[73] Assignee: Kimberly-Clark Worldwide, Inc., Neenah, Wis.

[21] Appl. No.: 281,548

[22] Filed: Jul. 27, 1994

Related U.S. Application Data

[62] Division of Ser. No. 448,177, Dec. 8, 1989, Pat. No. 5,360,419.

[51] Int. Cl.$^6$ .................... B05D 1/02; B05D 1/12; B05D 1/36
[52] U.S. Cl. .................... 427/180; 427/201; 427/202; 427/421; 427/333
[58] Field of Search ................. 427/195, 189, 427/201, 180, 421, 417, 202, 333; 604/367, 368, 370

[56] References Cited

U.S. PATENT DOCUMENTS

| | | | |
|---|---|---|---|
| 2,795,517 | 6/1957 | Lowe et al. | 427/333 |
| 3,587,579 | 6/1971 | Sabee | 128/287 |
| 3,636,952 | 1/1972 | George | 128/287 |
| 3,683,916 | 8/1972 | Mesek et al. | 128/287 |
| 3,720,562 | 3/1973 | Drelich | 156/291 |
| 3,881,490 | 5/1975 | Whitehead et al. | 128/287 |
| 3,890,974 | 6/1975 | Kozak | 128/287 |
| 3,901,238 | 8/1975 | Gellert et al. | 128/287 |
| 3,903,890 | 9/1975 | Mesek et al. | 128/287 |
| 3,955,577 | 5/1976 | Gellert et al. | 128/290 R |
| 3,961,125 | 6/1976 | Suminokura et al. | 428/261 |
| 3,978,257 | 8/1976 | Ring | 428/137 |
| 3,993,551 | 11/1976 | Assarsson et al. | 204/159.14 |
| 4,063,995 | 12/1977 | Grossman | 162/112 |
| 4,141,772 | 2/1979 | Buell | 156/227 |
| 4,217,078 | 8/1980 | Buell | 425/81.1 |
| 4,223,677 | 9/1980 | Anderson | 128/287 |
| 4,436,867 | 3/1984 | Pomplun et al. | 524/503 |
| 4,443,492 | 4/1984 | Roller | 427/44 |
| 4,447,570 | 5/1984 | Cook et al. | 524/127 |
| 4,522,967 | 6/1985 | Sheldon et al. | 524/377 |
| 4,573,989 | 3/1986 | Karami et al. | 604/381 |
| 4,623,688 | 11/1986 | Flanagan | 524/377 |
| 4,644,032 | 2/1987 | Keskey et al. | 524/549 |
| 4,690,679 | 9/1987 | Mattingly, III et al. | 604/383 |
| 4,883,478 | 11/1989 | Lerailler et al. | 604/360 |
| 4,914,170 | 4/1990 | Chang et al. | 526/240 |
| 4,948,575 | 8/1990 | Cole et al. | 424/44 |

OTHER PUBLICATIONS

Smith, et al. "Industrial & Engineering Chemistry", 51 (11), Nov. 1959 pp. 1361–1364.

"Equilibrium Study of Polymer–Polymer Complexation of Poly(methacrylic Acid) and Poly(acrylic Acid) with Complementary Polymers through Cooperative Hydrogen Bonding", *Journal of Polymer Science*: Polymer Chemistry Edition, vol. 17, No. 11, 3485–3498 (Nov. 1979) by Yoshihito Osada, Published by John Wiley & Sons, 1979.

"Some Factors Affecting the Molecular Association of Poly(ethylene Oxide) and Poly(acrylic Acid) In Aqueous Solution", *Journal of Polymer Science*: Part A, vol. 2, No. 2, pp. 845–851 (Feb. 1964) by F. E. Bailey Jr. et al.

"Study of Ternary Component Polymer Complexes of Poly(Methacrylic Acid) and Poly(Acrylic Acid) with Complementary Polymers", *Die Angewandte Makromolekulare Chemie* 116 (1983) 99–107 written by S. K. Chatterjee et al., and published by Huthig & Wepf Verlag, Basel in 1983.

(List continued on next page.)

*Primary Examiner*—Shrive Beck
*Assistant Examiner*—Fred J. Parker
*Attorney, Agent, or Firm*—Thomas J. Mielke

[57] ABSTRACT

An absorbent structure comprising a fibrous web of cellulosic material, a first complex forming material present within said web and a second complex forming material present within said web. When wetted, the first and second complex forming materials form a complex thereby providing the fibrous web of cellulosic material with improved integrity.

13 Claims, 2 Drawing Sheets

OTHER PUBLICATIONS

"Reversible Interpolymer Complexation between Poly(oxyethylene)–Based Amphiphilic Block Polymer and Poly(acrylic acid) at the Air–Water Interface", *Macromolecules*, vol. 22, No. 2 (Feb. 1989), by Masazo Niwa et al., published 1989 by American Chemical Society.

"Association Reactions for . . . Poly(alkylene Oxides) and Polymeric Poly(carboxylic Acids)", *Industrial and Engineering Chemistry*, vol. 51, No. 11, pp. 1361–1364, (Nov. 1959), by K. L. Smith et al.

"Thermal Equilibrium of the Intermacromolecular Complexes of Polycarboxylic Acids Realized By Cooperative Hydrogen Bonding", *Polymer Letters Edition*, vol. 14, No. 3, pp. 129–134 (Mar. 1976), by Yoshihito Osada et al.

ABSORBENT STRUCTURE POSSESSING IMPROVED INTEGRITY

CROSS-REFERENCE TO RELATED APPLICATION

This is a division of application Ser. No. 07/448,177, filed Dec. 8, 1989, now U.S. Pat. No. 5,360,419.

BACKGROUND OF THE INVENTION

1. Field of the Invention

The present invention relates to an absorbent fibrous web. Specifically, the present invention concerns an absorbent fibrous cellulosic web possessing improved integrity.

2. Description of the Related Art

Absorbent structures for the absorption of body fluids are known to those skilled in the art. As a general rule, such structures comprise a water-impervious backing sheet, an absorbent fibrous web, and a water-pervious body-side lining material. The fibrous web is sandwiched between the body-side liner and the backing sheet. The fibrous web is suitably formed from cellulosic material such as wood pulp fluff, cotton, rayon, and the like. Unfortunately, due to stresses placed on such fibrous webs during use, the webs have a tendency to separate into clumps of material. This is particularly true when the absorbent fibrous webs are wet. This clumping results from a tendency of the fibrous webs of cellulosic material to possess a relatively low degree of structural integrity. That is, the fibers of the web tend to separate easily thus allowing the webs to pull apart.

Means of enhancing the structural integrity of cellulosic fibrous webs are known. For example, U.S. Pat. No. 3,903,890 issued Sep. 9, 1975 to Mesek et al., is directed to a disposable diaper of simple construction. Mesek et al., describes improving the structural integrity of a fibrous web by applying a binder material to a surface of the fibrous web opposite a water-impermeable backing sheet. The binder material extends through the web thickness in spaced linear areas. The binder described may be either thermoplastic or thermosetting, and is preferably in the form of an aqueous emulsion or latex.

U.S. Pat. No. 4,573,989 issued Mar. 4, 1986 to Karami et al., is directed to a disposable diaper and method of manufacture. This reference describes spraying a binder between an absorbent fibrous web and a water-impervious backing sheet. The binder penetrates the fibrous web to adhere the web to the backing sheet. The presence of the binder material is described as rendering the pad highly tear resistant.

U.S. Pat. No. 3,978,257 issued Aug. 31, 1976 to Ring is directed to an internally adhesively bonded fibrous web. The web described by Ring has an adhesive uniformly disbursed in the X-Y direction of a fibrous web. The adhesive is not uniformly disbursed in the Z direction and is located primarily in an internal plane of the fibrous web. Thus, both outer surfaces of the web are generally adhesive free.

Unfortunately, as a general rule, when adhesives are used as described in the above references to enhance the structural integrity of a fibrous cellulosic web, the increase in integrity causes a decrease in the degree of softness or suppleness of the web. Obviously, when the fibrous webs are intended for use in products such as diapers, it is desirable that the fibrous web be highly supple, thus, increasing the comfort to a wearer. If the adhesive is not carefully selected, the adhesive may provide satisfactory structural integrity when the fibrous web is dry, but fail to provide desirable structural integrity when the fibrous web is exposed to a body fluid such as urine. Additionally, if the adhesive is hydrophobic in nature, application of the adhesive may deleteriously affect the absorbent characteristics of the fibrous web.

Accordingly, it is desirable to provide a fibrous web which possess both a high degree of wet and dry structural integrity and which maintains its absorbency and suppleness in both the dry and wet state.

Polymer complex formation between water-soluble polymers has been described. See for example, K. L. Smith et al., Industrial and Engineering Chemistry, 51 (11), 1361, (1959); Y. Osada, Journal of Polymer Science: Polymer Chemistry Edition, 17, 3485, (1979); S. K. Chatterjee, et al., Die Angewandte Makromolekulare Chemie, 116, 99 (1983). Polymer complex formation between water-soluble polymers generally results from the formation of extremely stable hydrogen bonds between the polymers when the polymers are in contact in an aqueous solution. In particular, poly acids, such as poly (acrylic acid) or poly (methacrylic acid), are reported to form complexes with polyethers such as poly (ethylene oxide) and polyamides such as poly (vinylpyrrolidone) or poly (ethyl oxazoline).

SUMMARY OF THE INVENTION

It is desirable to provide an absorbent structure comprising a fibrous web which web possesses improved wet and dry integrity. It is further desired to provide the fibrous web with improved wet and dry integrity without unacceptably affecting the suppleness or absorbency of the fibrous web.

These and other related goals are achieved in the present invention directed to an absorbent structure comprising a fibrous web of material. Present in the web are first and second complex forming materials. The first and second complex forming materials are capable, in the presence of water, of forming a complex. In one embodiment, the complex is formed between water-soluble first and second complex forming materials which materials are in solution. The complex precipitates out of solution and engulfs a portion of the fibers of the fibrous web, thus, providing the web with increased integrity.

In one preferred embodiment of the present invention, there is provided an absorbent structure comprising a fibrous web of material. Present within the fibrous web are first and second complex forming materials. At least one of the first or second complex forming materials is in the form of a water-soluble polymeric thermoplastic solid. The solid polymeric thermoplastic water-soluble complex forming material serves to bind the individual fibers of the fibrous web together, thus providing the web with enhanced dry integrity. When the web is wetted, the first and second complex forming materials form a complex. The complex provides the fibrous web with enhanced wet integrity. The absorbent structures of the present invention are suitably employed in absorbent personal care products such as diapers, sanitary napkins, tampons, bandages, adult incontinence products, and the like.

DETAILED DESCRIPTION OF THE PREFERRED EMBODIMENT

Figure 1:
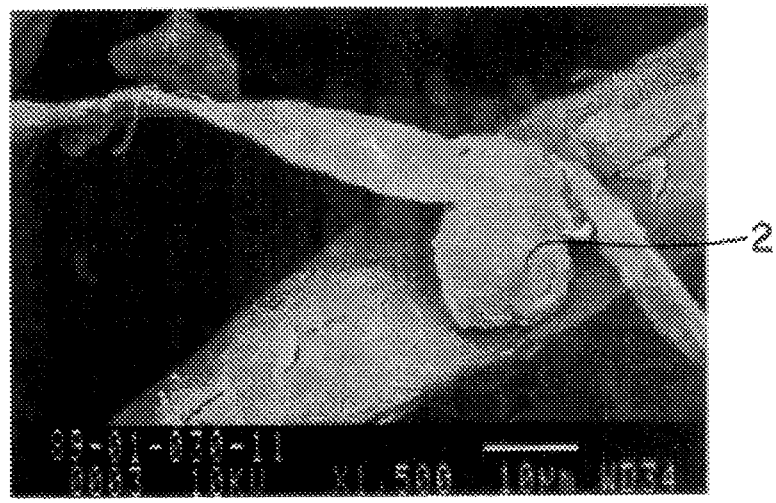
FIG. 1 is a photomicrograph of one embodiment of an absorbent structure according to the present invention in a dry state.

The present invention relates to an absorbent structure. The absorbent structure comprises a fibrous web preferably of cellulosic material. While reference herein may be made to a cellulosic web, it is to be understood that other materials such as, for example, meltblown polyethylene or propylene, may be employed to form the web. Exemplary of the cellulosic fibrous material suitable for use in the present invention is comminuted wood pulp known as wood pulp fluff. Also suitable for use are cotton, rayon, and the like. When wood pulp fluff is employed to form the cellulosic fibrous web, the wood pulp fluff may be formed from bleached or unbleached hardwood pulp, bleached or unbleached softwood pulp, or a combination of hardwood and softwood pulps. Suitable wood pulp fluff webs have a density of from about 0.05 to about 4.0 grams per cubic centimeter, preferably from about 0.1 to 2.0 grams per cubic centimeter measured under a load of 0.2 pounds per square inch.

Present in the fibrous web are first and second complex forming materials. At least one and preferably both of the complex forming materials are water-soluble. As used herein, the term "water-soluble" refers to materials which dissolve completely in water to give a true solution as opposed to materials which form a latex or suspension of undissolved particles. The complex forming materials generally have weight average molecular weights ($M_w$) within the range of from about 10,000 to about 20,000,000.

As used herein, the term "complex forming material" refers to material which, when in the presence of water, is capable of forming a complex with a second material. As used herein, the term "complex" refers to a situation wherein two molecules are linked to one another through the presence of bonds, such as hydrogen bonds, ionic bonds or the like.

Those skilled in the art will recognize that the term "hydrogen bond" refers to an attractive force which occurs in polar compounds when a hydrogen atom of one molecule is attracted to two unshared electrons of another molecule. Hydrogen bonds form between a hydrogen atom which is possessed of a partial positive charge and a second atom possessed of a partial negative charge due to the presence of the two unshared electrons. Similarly, those skilled in the art recognize that the term "ionic bond" refers to the electrostatic attraction among oppositely charged ions.

Reference to the first complex forming material refers to a material having molecules which possess one or more atoms having at least a partial positive charge. Reference to the second complex forming material refers to a material having a molecule including one or more atoms which possess at least a partial negative charge. Reference to "at least a partial" positive or negative charge encompasses both the situation wherein the complex forming materials have a partial positive or negative charge as well as the situation wherein one or more of the complex forming materials have a full positive or negative charge.

When the complex forming materials have a partial charge, the complex formed by such materials generally forms as a result of hydrogen bonding. When the polymeric complex forming materials have a full charge, the complex formed by such materials generally forms as a result of ionic bonding.

When the first and second complex forming materials of the present invention are brought together in the presence of water, the two materials suitably form a complex due, for example, to hydrogen bonding occurring between the two materials. In some instances, the hydrogen bonds formed are extremely strong and stable (for hydrogen bonds) and, under proper pH conditions, cause the complex formed from the two materials to precipitate out of solution as a solid. It is generally preferred that such precipitated solid complexes have a glass transition temperature of about −50° C. to about 100° C.

Any material capable of forming complexes such as those described above and possessing an atom having at least a partial positive charge is suitable for use as the first polymeric complex forming material of the present invention. Exemplary of water-soluble materials suitable for use as the first complex forming material are polyacids, including poly (acrylic acid) or poly (methacrylic acid), carboxymethylcellulose, methyl vinyl ether/maleic acid copolymers, ethylene/maleic acid copolymers, ethylene/acrylic acid copolymers, ethylene/methacrylic acid copolymers, styrene/maleic acid copolymers; and the like. Such polyacids suitably have an average molecular weight ($M_w$) of from about 10,000 to about 20,000,000.

Any material capable of forming the complexes described above and possessing an atom having at least a partial negative charge is suitable for use as the second complex forming material of the present invention. Exemplary of water-soluble materials suitable for use as the second complex forming materials are the polyethers, polyamides and quaternary amines. Suitable polyethers include poly (ethylene oxide), poly (propylene oxide), ethylene oxide/propylene oxide copolymers, poly (tetramethylene oxide), poly (vinyl methyl ether), and the like. Suitable polyamides include poly (ethyl oxazoline), poly (vinylpyrrolidone), copolymers of poly (vinylpyrrolidone), poly (amidoamine), poly (acrylamide), polyethylene amine, and the like.

It is to be understood, that the materials described as suitable for use as the first and second complex forming materials may be used individually or in combination. Additionally, other water-soluble materials, plasticizers or modifiers may be included with the first and second complex forming materials in the fibrous web. Exemplary of other suitable materials which may be included in the fibrous webs of the absorbent structures of the present invention are polyvinyl alcohol, glycerin, sorbitol, polyethylene glycol, polypropylene glycol, low molecular weight polyethylene oxide, and the like.

The first and second complex forming materials of the present invention can be applied to the fibrous webs of cellulosic material in a variety of manners. For example, the first and second complex forming materials may, if they are water-soluble, be individually dissolved in water to form two solutions. The solutions may then be applied by spraying or other means to the fibrous cellulosic web. Alternatively, one of the complex forming materials may be applied to the web as a solid with the other complex forming material being water-soluble and applied to the web as an aqueous solution. Alternatively, both the first and second complex forming materials may be applied to the fibrous web of cellulosic material in the form of solid particles. When either or both of the first and second complex forming materials are applied to the web as a solid, they are suitably in the form of discrete particles having a maximum cross-sectional diameter of from about 5 to about 100 micrometers. The particles may be applied to the web after formation or, as is generally preferred, may be mixed with the fibrous material from which the web is formed prior to formation of the web.

In one preferred embodiment of the present invention, at least one of the complex forming materials is a polymer and is applied to the web as a solid and is a thermoplastic solid having a Vicat softening point (ASTM test method D-1525) within the range of from about 30° C. to about 200° C., preferably within the range of from about 50° C. to about 100° C. The other complex forming material may be polymeric and may be applied to the web either in solution or as a thermoplastic or thermosetting solid. If both complex forming materials are polymeric, thermoplastic solids, they may both have Vicat softening points within the defined ranges or, only one may have such a softening point.

FIG. 1 is a photomicrograph showing a solid thermoplastic particle 2 of complex forming material adhering two fibers together. The structure is in a dry state with the thermoplastic particle improving the dry integrity of the web.

Figure 2:
FIG. 2 is a photomicrograph of one embodiment of an absorbent structure according to the present invention in a wet state.

FIG. 2 is a photomicrograph of the structure of FIG. 1 in a wet state. FIG. 2 illustrates a complex 4 which has formed and precipitated out of solution. The complex 4 is seen to adhere two fibers together thus providing wet integrity to the structure.

In the case where one of the complex forming materials is applied to the web in the form of a polymeric thermoplastic solid, having a Vicat softening point within the defined ranges, the web is preferably elevated to a temperature such that the thermoplastic solid softens to an extent such that when the web is subsequently cooled, the thermoplastic solid forms physical bonds between some of the individual fibers of the fibrous web. The elevation in temperature may occur after or concurrently with the application of the thermoplastic solid to the web. Suitably, the necessary degree of softening of the solid polymeric thermoplastic complex forming material occurs when the material and web are elevated to a temperature between about 30° C. and about 200° C. In this manner, the dry integrity of the web is enhanced by the presence of the physical bonds formed by the thermoplastic solid polymeric complex forming material.

As discussed above, the other complex forming material may be polymeric and may be present in the web in the form of a solution or thermoplastic or thermosetting solid. It may be desirable for both the first and second complex forming materials to be polymeric and in the form of a water-soluble thermoplastic solid capable of forming physical bonds between the fibers of the web upon elevation to a temperature at which both polymers soften and subsequent cooling of the web. It is to be understood that the fibrous webs containing the first and second polymeric complex forming materials should not be elevated above a temperature at which an undesirable degree of thermal degradation occurs in either the cellulose fibers or the polymeric complex forming materials.

The wet integrity of the structures according to the present invention is enhanced through complex formation. Specifically, in the presence of water (moisture) and when the first and second complex forming materials are in close proximity, the described complex is formed. More specifically, it is believed that upon wetting, at least a portion of the water-soluble first or second complex forming material goes into solution. When both the first and second complex forming materials are water-soluble, at least a portion of both complex forming materials may go into solution. In solution, the two materials contact one another thereby forming the described complex. Due to the presence of the at least partial negative and partial positive charges, the complex forming materials may similarly be capable of forming a bond, such as a hydrogen bond, with the cellulose fibers of the cellulosic fibrous web. Thus, the wet integrity may be at least partially provided by the formation of a bond involving the cellulose fibers, the first water-soluble complex forming material and the second water-soluble complex forming material. The formation of the complex between the first and second complex forming materials within a desirable pH range causes such complex to precipitate out of solution around portions of adjacent individual fibers of the web. The precipitated complex thereby effectively adheres such fibers together. This in turn serves to increase the integrity of the fibrous web.

It is to be appreciated that in certain embodiments of the present invention the mechanism by which dry integrity is provided to the fibrous web differs from that by which wet integrity is provided to the web. Specifically, dry integrity may be provided by the presence of physical bonding between the cellulose fibers and the individual, noncomplexed thermoplastic solid polymeric complex forming material. Wet integrity may be provided by formation of the above described precipitated complex through hydrogen bonding between the fibers and the complex and through engulfment and adhesion of the fibers by the precipitated complex.

In another embodiment of the present invention, the water-soluble complex forming materials are polymeric and are applied to the web in the form of individual aqueous solutions. In this embodiment, when the individual solutions contact each other in the fibrous web of cellulosic material, the complex between the first and second water-soluble complex forming materials is immediately formed. Formation of the complex within a desirable pH range causes the complex to precipitate out of solution as a solid complex which solid complex is adhered to the cellulose fibers. Since the complex itself is generally thermoplastic, it can be further heat treated to enhance the dry integrity. It is to be understood that in this instance, both the dry and wet integrity will be enhanced through the presence of the precipitated complex.

When the complex formed is formed through the creation of hydrogen bonds, heating of the formed complex (while in solution) may cause the hydrogen bonds to break and the complex to dissociate. Once dissociated, the first and second complex forming materials will behave as if they had been applied separately to the fibrous web. Additionally, when the complex is formed through the creation of hydrogen bonds, the complexes can be caused to dissociate, in an aqueous environment, by raising the pH of the environment. For example, if the first complex forming agent is a water-soluble polyacrylic acid and the second complex forming material is a water-soluble polyethylene oxide, the complex will form in an aqueous solution having a pH in the range of from about 2 to about 10 and will dissociate when the pH is raised to within the range of from about 10 to about 14. Moreover, such a complex may be soluble in the aqueous solution at pH's within the range of from about 4 to about 10 but may be found to precipitate out of solution at pH's less than about 4. It is to be understood that the pH dependent behavior of a given complex will vary depending on the molecular weights of the first and second complex forming materials.

As it is used herein, reference to the term "dry integrity" does not necessarily require that the fibrous web be completely free of moisture. In the situation wherein the first and second complex forming materials are applied to the web in the form of individual solutions, the solutions can be applied at levels such that the fibrous webs will be tactually perceived as being generally dry, but will nonetheless contain sufficient moisture to form and maintain the presence of the complexes. Thus, reference to a dry fibrous web is intended to encompass fibrous webs containing up to about 25 percent (25%) moisture. Once the complexes are formed, they will remain in solid form regardless of the moisture content but may, as discussed above, be dissociated by the application of heat or by raising the pH.

As a general rule, the total amount of first and second complex forming material present in the fibrous webs will be within the range of from about 0.001 to about 10 weight percent, preferably from about 0.05 to about 5 weight percent based on total weight of the fibrous web. As a general rule, the ratio of first complex forming material to second complex forming material will be within the range of from about 0.1:10 to about 10:0.1, preferably from about 1:1.5 to about 1.5:1.

The inventors have discovered that the dry and wet integrity of cellulosic fiber webs can be significantly enhanced according to the present invention without increasing the stiffness of the fibrous webs to an undesirable degree. This is a significant advance over known methods of increasing fibrous web integrity. When it is desired to maintain the suppleness of the cellulosic fibrous webs, the total amount of first and second complex forming material present in the webs will suitably be within the range of from about 0.001 to about 2.0 weight percent based on total weight of the fibrous web. Moreover, the first and second complex forming materials can be selected so that the glass transition temperature of the formed precipitated complex is within the range of from about −50° C. to about 20° C., preferably from about 0° C. to about 20° C. For example, precipitated complexes formed from water-soluble polyacrylic acid (weight average molecular weight 1,200,000) and polyethylene oxide (weight average molecular weight 150,000) have a glass transition temperature of about 13° C. By keeping the glass transition temperature of the complex below about 20° C., the complexes are soft at room temperatures thus helping to maintain the suppleness of the webs in which they are located.

At loadings greater than about 2 weight percent, based on total weight of the web, the presence of the complex forming materials can impart significant stiffness to the cellulosic fibrous webs. At loadings greater than about 2.0 weight percent, webs can be formed having sufficient stiffness to form three-dimensional structures. That is, the presence of the complex forming material imparts a degree of stiffness sufficient to allow the cellulosic fibrous webs to be formed into three dimensional structures.

Generally, when relatively stiff cellulosic fibrous materials are desired to be formed, the complex forming material is polymeric and is present in the web in an amount which is within the range of from about 2.0 to about 10 weight percent based on total weight of the fibrous web. Additionally, if it is desired to produce a relatively stiff structure, the complex forming materials can be selected so that the glass transition temperature of the precipitated complex is within the range of from about 20° C. to about 100° C. Thus, at room temperature, the complex is in a generally glassy, brittle state thus adding to the stiffness of the product.

It has been discovered that the complex forming materials of the present invention can be selected so that they do not affect the absorbency of the cellulosic fibrous webs to an undesirable degree. In the past, many of the adhesive binders applied to cellulosic fibrous webs have deleteriously affected the absorbency of the webs due to the fact that the known adhesive binders tend to be hydrophobic. Clearly, due to the water-soluble nature of the complex forming material(s) of the present invention and their ability to form a complex through hydrogen or ionic bonds, they are generally hydrophilic. Thus, even when the complex forming materials are present in loadings sufficient to allow formation of three-dimensional structures from the webs, the hydrophilic nature of the complex forming materials do not substantially lower the absorbency of the cellulosic fibrous webs.

Moreover, the complex forming materials of the present invention have been shown to improve the vertical wicking capacity, and distribution properties of a web containing the complex forming materials. The improvements to vertical wicking capacity, and distribution are believed to be a result of the improved integrity which the complex forming materials impart to the webs. Specifically, it is believed that the improved integrity serves to prevent or reduce the amount of interfiber collapse which normally results when known webs are wetted.

The absorbent structures of the present invention are suitably incorporated into diapers. As a general rule, diapers comprise a backing sheet formed from a water-impervious material, an inner water-pervious body-side lining material adapted to contact the skin of the wearer, and an absorbent materials such as the absorbent structures of the present invention sandwiched therebetween. In use, a body fluid, such as urine, insults the body-side lining material, passes through the body-side lining material and is absorbed by the absorbent material. The water-impervious backing sheet prevents liquid from passing externally of the diaper structure. Diapers and similar products are generally described in U.S. Pat. Nos. 4,710,187 issued Dec. 1, 1987 to Boland et al.; 4,762,521 issued Aug. 9, 1988 to Roessler et al.; 4,770,656 issued Sep. 13, 1988 to Proxmire et al.; and 4,798,603 issued Jan. 17, 1989 to Meyer et al., which references are incorporated herein by reference.

When the absorbent structures of the present invention are to be incorporated into a diaper structure, it is often desired that the absorbent structures possess a desirable degree of wet and dry integrity as well as being free from an undesirable amount of stiffness.

One method of quantifying the stiffness of a given absorbent structure is the Gurley Stiffness test. The method of determining the Gurley Stiffness value is set forth in greater detail in connection with the examples which follow. As a general rule, when the absorbent structures of the present invention are to be employed in diapers, it is desired that the Gurley Stiffness of the absorbent structures be within the range of from about 100 to about 5,000 preferably within the range of from about 900 to about 1600 milligrams.

One method of quantifying the wet and dry structural integrity of the absorbent structures of the present invention is to determine the tangent modulus, yield strength and yield elongation of the structures. The exact method of measuring the described mechanical properties is set forth below in connection with the examples. The various mechanical properties are determined on both wet and dry samples. As a general rule, the tangent modulus (determined as set forth in connection with the examples) for dry samples according to the present invention is suitably within the range from about 500 to about 2000 pounds per square inch, preferably from about 700 to about 1000 pounds per square inch. The tangent modulus (determined as set forth in connection with the examples) for wet samples according to the present invention is suitably within the range from about 75 to about 250 pounds per square inch, preferably from about 100 to about 200 pounds per square inch.

The yield strength (determined as set forth below in connection with the examples) for dry structures according to the present invention is suitably within the range of from about 25 to about 75 pounds per square inch, preferably from about 30 to about 50 pounds per square inch. The yield strength (determined as set forth below in connection with the examples) for wet structures according to the present invention is suitably within the range of from about 10 to about 20 pounds per square inch, preferably from about 12 to about 18 pounds per square inch. The yield elongation (determined as set forth below in connection with the examples) for dry structures according to the present invention is suitably within the range from about 3 to about 10 percent, preferably from about 5 to about 8 percent. The yield elongation (determined as set forth below in connection with the examples) for wet structures according to the present invention is suitably within the range from about 6 to about 12 percent, preferably from about 8 to about 11 percent.

The preferred ranges discussed above generally represent a significant improvement over cellulosic fibrous webs not containing the complex forming materials of the present invention. For example, cellulosic fibrous webs alone, without addition of the complex forming materials of the present invention have been found to have a tangent modulus of about 350 pounds per square inch when dry and when wet, of about 65 pounds per square inch. Thus, it is seemed that by addition of the first and second complex forming materials of the present invention, a significant increase in tangent modulus (strength) is achievable. This increase in tangent modulus is achievable without introducing into the cellulosic fibrous webs an undesirable degree of stiffness.

Those skilled in the art will recognize that in many instances it is desirable to incorporate a water-swellable, water-insoluble polymeric material into absorbent products such as diapers, sanitary napkins, adult incontinence products, bandages, and the like. As used herein, reference to water-swellable, water-insoluble polymeric materials is intended to refer to polymeric materials which are capable of absorbing at least about ten times their weight in water. Such water-swellable, water-insoluble polymeric materials are known to those skilled in the art. Exemplary of such materials are carboxymethyl cellulose, alkaline metal salts of poly acrylic acids, poly acrylamides, poly vinyl alcohol, ethylene maleic anhydride copolymers, poly vinyl ethers, hydroxypropylcellulose, poly vinyl morpholinone, polymers and copolymers of vinyl sulfonic acid, poly acrylates, poly acrylamides, poly vinyl pyridine, and the like. Other suitable polymers include hydrolyzed acrylonitrile grafted starch, acrylic acid grafted starch, and isobutylene maleic anhydride copolymers, and mixtures thereof. Such polymeric materials are preferably lightly cross-linked to render the materials substantially insoluble.

When such water-swellable, water-insoluble polymeric materials are incorporated into cellulosic fibrous webs, the polymeric materials may be applied to the cellulosic webs in the form of discrete particles and are generally applied in an amount of from about 5 to about 75 weight percent based on total weight of the web and polymeric material. Such discrete particles have been found to separate out and migrate through the cellulosic fibrous webs. This is often undesirable. Accordingly, the inventors have discovered that it is possible to employ the complex forming materials of the present invention to not only increase the structural integrity of the cellulosic fibrous webs, but also to minimize migration of the water-swellable, water-insoluble polymeric materials through the fibrous webs. For example, when the cellulosic fibers are bonded together the bonded fibers may serve to entrap or encage the water-swellable, water-insoluble polymeric materials. Additionally, when at least one of the complex forming materials of the present invention is a solid polymeric thermoplastic material used to physically adhere the cellulose fibers together, water-swellable, water-insoluble polymeric material copresent in the fibrous webs will also be adhered in a specific location within the fibrous webs by the polymeric thermoplastic complex forming material.

Alternatively, a tacky binder may be applied to the water-swellable, water-insoluble material to adhere the solid complex forming material to the particles of water-swellable, water-insoluble polymer. In this manner, when the solid thermoplastic complex forming materials adhere to the cellulose fibers, the water-swellable, water-insoluble polymers will similarly be adhered to a specific location within the cellulose fiber webs.

The present invention can best be understood by reference to the following examples (including comparative examples) which examples are not intended to limit, in any way, the scope of the invention as set forth in the claims.

EXAMPLES

The following test methods were used in connection with all of the following examples. All thickness, density and/or basis weight determinations reported or required by the test procedures are determined under a 0.2 pounds per square inch applied pressure (load).

GURLEY STIFFNESS

The Gurley Stiffness is a measure of the ability of a sample to resist an applied bending force. The determinations are made on a Gurley Stiffness Tester available from the W & L. E. Gurley Company, Troy, N.Y.

Test specimen 3.5 inches long and 1 inch wide are prepared by cutting. The samples are clamped in the Gurley Stiffness Tester and tested according to the operating procedure provided with the tester employing a weight of 5 grams located 4 inches from the center of the sample. The results of the test are then converted to milligrams.

VERTICAL-FLUID INTAKE AND FLOWBACK EVALUATION (V-FIFE)

Figure 3:
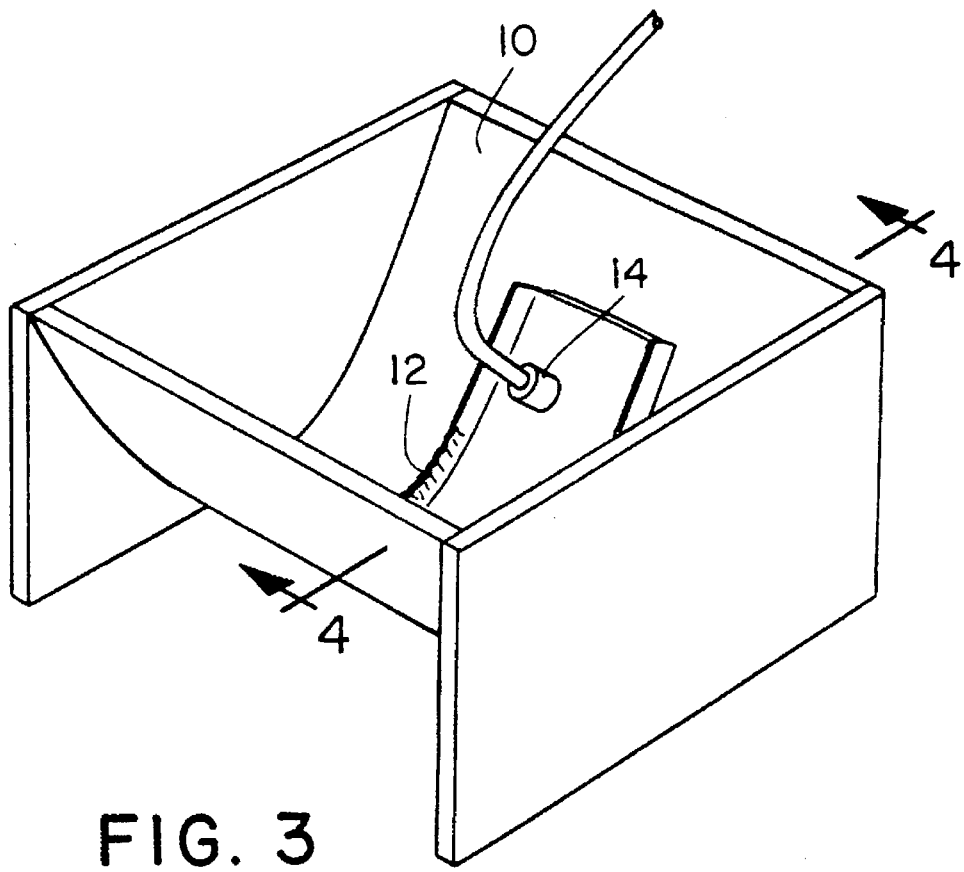
FIG. 3 is a perspective view of a testing apparatus used to evaluate vertical fluid intake and flow back of absorbent structures according to the present invention.
Figure 4:
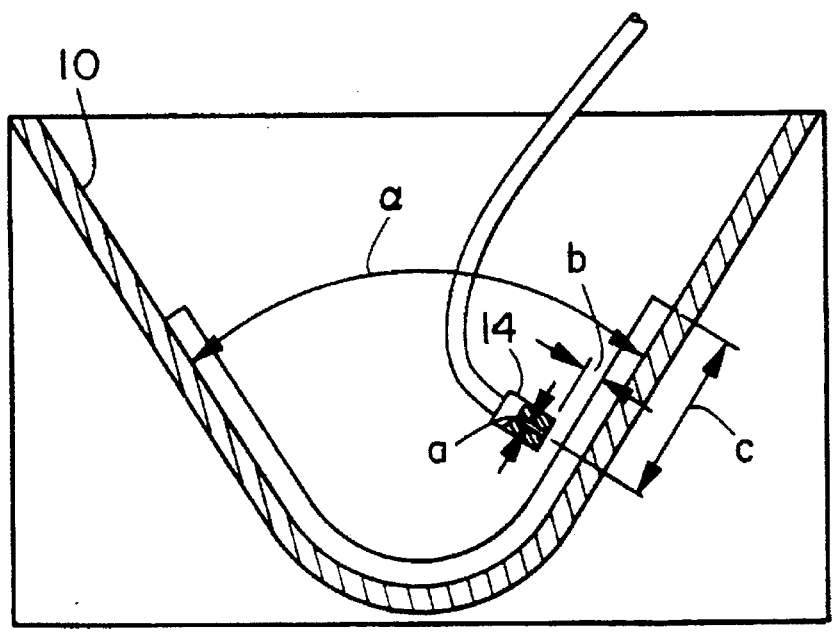
FIG. 4 is a cross-sectional view taken along line 4—4 of FIG. 3.

Referring to FIGS. 3 and 4, a sample (5 inches by 15 inches) is placed in a trough 10 with an included angle, alpha of 60°, such that all "runoff" is contained on the bodyside of the sample using suitable dams 12 along the sample edges. The total time to imbibe an insult is measured. Fluid is delivered from a nozzle 14 having 4 mm. diameter (a) which is attached to a peristaltic pump equipped with a pulse suppressor. The nozzle is placed a distance (b) of 6 mm. from the absorbent surface of the sample, a distance (c) of about 6.3 cm from the end of the sample and at a perpendicular angle. Fluid is dispensed at an average rate of 12 mL/sec. for 5 seconds during each insult (total each insult, 60 ml).

The fluid volume per insult (60 ml) is divided by the time elapsed between initial fluid contact and disappearance beneath the absorbent surface to determine the reported fluid intake rate. Samples are allowed to equilibrate 15 minutes between insults. A total of 3 insults are delivered. The fluid employed is a synthetic urine produced as follows:

To 900 milliliters of distilled water are added, in the following order, 0.31 grams of monobasic calcium phosphate monohydrate ($CaH_4(PO_4)_2H_2O$), 0.68 grams monobasic potassium phosphate ($KH_2PO_4$), 0.48 grams magnesium sulfate heptahydrate ($MgSO_4\,7H_2O$) 1.33 grams potassium sulfate ($K_2SO_4$), 1.24 grams tribasic sodium phosphate dodecahydrate ($Na_3PO_4\,12H_2O$), 4.4 grams sodium chloride (NaCl) 3.16 grams potassium chloride (KCl), 0.4 grams sodium azide ($NaN_3$), 8.56 grams urea ($CO(NH_2)_2$), and 0.1 grams pluronic 10R8 (a non ionic surfactant commercially available from BASF-Wyandotte Corporation). Each of the components is added to the 900 milliliters of distilled water in the order given with each component being dissolved before the next component is added. The resulting solution is then diluted to 1 liter.

VERTICAL WICKING CAPACITY/FLUID DISTRIBUTION

U-shaped

A test sample 3 inches wide and 15 inches long is cut from the sample to be tested. The test sample is mounted on a lucite plate that is ⅜ inch thick, 13 inches wide and 14 inches long. The test sample is symmetrically wrapped on the plate such that it is laid against one longitudinal surface, bent around one edge of the plate and laid against the opposite longitudinal surface of the plate. In this manner, approximately ½ the length of the test sample is located against one longitudinal surface of the plate with the other half of the test sample being located against the opposite longitudinal surface of the test plate. The test sample is totally supported on its outer surface against the test plate by a ten mesh nylon screen. The opposite longitudinal ends of a sample are fastened to the lucite plate by a clamp or similar means which holds the screen and the test sample against the plate near the top of the sample.

The plate is suspended vertically over a fluid bath contained in a tray with the longitudinal dimension of the test sample perpendicular to the fluid surface. The fluid is then brought into contact with the test sample by immersing the lower edge of the plate in the fluid so that the U-shaped test sample covering the edge of the lucite plate is slightly immersed. The amount of fluid absorbed as a function of time is recorded at several time intervals for the 15 minute duration of the test. The fluid employed is the synthetic urine hereinbefore described. The amount of fluid absorbed is calculated by weighing and is reported as grams of fluid absorbed per unit basis weight of 1 gram per square centimeter per unit width (1 inch).

J-shaped

A test sample 5½ inches wide and 15 inches long is cut from the sample to be tested. The test sample is mounted on a lucite plate that is ¼ inch thick, 6 inches wide and 16 inches long. The test sample is wrapped on the plate such that it is laid against one longitudinal surface, bent around one longitudinal edge of the plate and laid against the opposite longitudinal surface of the plate. The test sample is asymmetrically wrapped such that 4¾ inches of the length of the test sample are on one side of the plate and about 10 inches of the length of the test sample are on the opposite side of the plate. The test sample is totally supported on its outer surface against the test plate by a ten mesh nylon screen. The opposite longitudinal ends of the sample are fastened to the lucite plate by a clamp or similar means which holds the screen and the test sample against the plate near the top of the sample.

The plate is suspended vertically over a fluid bath contained in a tray with the longitudinal dimension of the test sample perpendicular to the fluid surface. The fluid is then brought into contact with the test sample by immersing the lower edge of the plate in the fluid so that the portion of the test sample covering the edge of the lucite plate is slightly immersed. The amount of fluid absorbed as a function of time is recorded at 15 seconds and 15 minutes. The fluid employed is the synthetic urine hereinbefore described. The amount of fluid absorbed is calculated by weighing and is reported as grams of fluid absorbed per gram of test sample. The 15 second value is believed to be indicative of the rate of the test sample.

The fluid distribution data is determined for the J-shaped samples in the following manner. The test sample is removed from the plate at the end of 15 minutes and laid horizontally on a 5½ inch by 15 inch cutting die which is segmented into 9 zones of about 1.7 inches each. The cutting die includes cutting edges across the die width and around the outer perimeter. Several quick blows with a mallet divide the 5½ inch wide absorbent strip along the longitudinal axis into nine segments (zones). Segment (zone) 1 corresponds to the longitudinal end of the sample on the short (4¾ inch) side of the lucite plate. Segment (zone) 9 corresponds to the longitudinal end of the sample on the long (10 inch) side of the lucite plate. The segments are weighed, oven dried, reweighed and the fluid pickup determined on a gram of fluid per gram of fiber basis (corrected for deposited solids from the fluid).

TANGENT MODULUS, YIELD STRENGTH, YIELD ELONGATION

The mechanical strength properties are determined on a tensile tester commercially available from Sintech, Staughton, Mass. The referenced tensile tester employs computer software specifically designed to calculate the reported mechanical properties. The test specimen employed is 5.08 centimeters wide, and 7.62 centimeters long. The testing procedure employed is that set forth by the manufacturer of the referenced tensile tester. The Yield strength refers to the strength at 95% of break and is determined at a cross head speed of 300 millimeters per minute. The Yield elongation is that elongation occurring at 95% of break and is determined at a cross head speed of 300 millimeters per minute. The tangent modulus is the slope of the stress-strain curve when the sample is elongated at a rate of 300 millimeters per minute.

DRYER INTEGRITY TEST

The relative structural integrity of various test webs is determined according to the following process. Dry samples 5.5 inches wide and 15 inches long are cut from the webs to be tested. The test samples are weighed. The samples are folded in half (longitudinal ends are brought together) and the ends stapled. The samples are then placed in a plastic bag (12 inches wide and 21 inches long). Air is blown into the bag and the bag sealed trapping as much air as possible inside the bag. Four such sample-containing bags are placed in a standard clothes dryer commercially available from Sears Roebuck Company under the trade designation Lady Kenmore™. The dryer is set to air fluff only (no heat) and allowed to spin for five (5) minutes. The samples are removed from the dryer. The material which has separated from the main body of the sample is removed from the bag and placed in a tared container. The container and material are dried in an oven for about two hours at a temperature of about 103° C. The weight of the material which separated from the sample is then determined and reported as a percent of total sample weight. The lower the weight of the material which separated from the sample the better the integrity of the sample.

The method of testing wet samples is the same as set forth above, except that 80 milliliters of synthetic urine (as described above) is applied to the test sample prior to folding the sample in half. The synthetic urine is applied to the sample in an area 5 inches from each longitudinal end and 1 inch from the sides. The synthetic urine is applied with the sample laying flat, at a rate of 1 milliliter per second.

EXAMPLE 1

Test samples according to the present invention are prepared by forming a mixture of bleached softwood pulp fluff and varying amounts of a 1:1 blend of a water-soluble polyacrylic acid (first complex forming material) commercially available from the B. F. Goodrich Company under the trade designation Carbopol 674 and a water-soluble polyethylene oxide (second complex forming material) commercially available from the Union Carbide Company under the trade designation Polyox WSR-N80.

To form the samples according to the present invention the mixture of the first and second complex forming material and wood pulp fluff, are airlayed into fibrous webs and densified to a density of about 0.14 grams per cubic centimeter. The specific amounts of first and second complex forming materials employed are set forth in Table 1, which follows. Reference to the percent of complex forming material refers to the weight percent of the 1:1 mixture of polyacrylic acid and polyethylene oxide based on total absorbent structure weight. A control sample is prepared by airlaying wood pulp fluff into a fibrous web and densifying said web. Both the control samples and the samples with complex forming material present therein, are thermally debulked in a heated press (such as a Dake press) at a temperature of 250° F. using sufficient pressure to achieve a density of 0.14 grams per cubic centimeter.

The control and test samples prepared as described above are then subjected to a variety of physical property determinations. The results of these physical property determinations are set forth in Table 1.

TABLE 1

| | Percent CFM[1] | | | | |
|---|---|---|---|---|---|
| | 0.0* | 0.15 | 0.3 | 0.5 | 1.4 | 2.8 |
| Gurley Stiffness[2] | 508 | 704 | — | — | 2430 | 2400 |
| Tangent Modulus[3] | | | | | | |
| dry | 354 | — | — | 1030 | 2120 | — |
| wet | 64.1 | — | — | 148 | 186 | — |
| Yield Strength[4] | | | | | | |
| dry | 21.1 | — | — | 28.1 | 51.1 | — |
| wet | 8.8 | — | — | 11.9 | 12.5 | — |
| Yield Elongation[5] | | | | | | |
| dry | 13.0 | — | — | 6 | 5 | — |
| wet | 12.0 | — | — | 11 | 9 | — |
| Dryer Integrity[6] | | | | | | |
| dry | 1.97 | 0.13 | — | — | 0 | 0.06 |
| wet | 25.6 | 18.7 | — | — | 0 | 0 |
| Vertical Wicking Capacity[7] | | | | | | |
| 15 sec | 2.83 | 2.68 | — | — | 2.60 | 2.39 |
| 15 min | 3.96 | 5.67 | — | — | 5.82 | 5.94 |
| Fluid Distribution[8] zone: | | | | | | |
| 1 | 1.1 | — | 2.6 | — | — | — |
| 2 | 2.5 | — | 3.8 | — | — | — |

TABLE 1-continued

| | Percent CFM[1] | | | | |
|---|---|---|---|---|---|
| | 0.0* | 0.15 | 0.3 | 0.5 | 1.4 | 2.8 |
| 3 | 6.1 | — | 6.7 | — | — | — |
| 4 | 8.4 | — | 8.2 | — | — | — |
| 5 | 8.7 | — | 8.9 | — | — | — |
| 6 | 9.0 | — | 8.8 | — | — | — |
| 7 | 6.7 | — | 8.0 | — | — | — |
| 8 | 4.2 | — | 5.9 | — | — | — |
| 9 | 3.4 | — | 3.8 | — | — | — |

—Not determined
*Not an example of the present invention
[1] Weight percent complex forming materials based on total absorbent structure weight
[2] Reported in milligrams
[3] Reported in pounds per square inch.
[4] Reported in pounds per square inch.
[5] Reported as percent of elongation occurring at 95% of break.
[6] Reported as weight percent of starting sample.
[7] Reported in grams of liquid absorbed per gram of sample weight, measured and reported at 15 seconds and 15 minutes.
[8] Reported as grams of absorbed liquid per gram of sample weight.

As can be seen from reference to Table 1, addition of the complex forming materials according to the present invention does not unacceptably increase the Gurley Stiffness Values compared to the control sample for the CFM concentrations tested. Nonetheless, the data for Tangent Modulus, Yield Strength, Yield Elongation and Dryer Integrity indicates that the strength of the samples containing the complex forming materials of the present invention is improved compared to the control sample. Additionally, review of the vertical wicking capacity and fluid distribution data indicates that this improvement in strength is achieved without unacceptably, deleteriously affecting the absorbent properties of the structures. In fact, the structures according to the present invention are seen to possess improved vertical wicking properties and improved fluid distribution at distances remote from the point of liquid contact. Thus, it is seen that the present invention produces an absorbent structure possessing improved integrity and absorbent/transfer properties but which is not undesirably stiffer when compared to a control sample not containing the complex forming materials of the present invention.

EXAMPLE 2

An aqueous solution of complex forming material according to the present invention is prepared as follows: Solution A is prepared by forming an aqueous solution containing 6 weight percent of a water-soluble polyacrylic acid (first complex forming material) commercially available from Alco Chemical Corporation under the trade designation Alcosperse 404 (molecular weight of 60,000) and 4 weight percent of a water-soluble polyvinyl alcohol commercially available from E. I. DuPont DeNemours Corporation under the trade designation Elvinol 75-15. Solution B is formed by adding 1 weight percent of sodium chloride based on total weight of solution B to an amount of solution A. Solution C is a 0.5 weight percent aqueous solution of a water-soluble polyethyloxazoline (second complex forming material) commercially available from the Dow Chemical Company under the trade designation PEOX.

Samples of an airlayed web of wood pulp fluff containing a starch grafted polyacrylic acid superabsorbent material commercially available from the Hoechst Celanese Corporation under the trade designation IM5000 are provided. The webs have a basis weight of 800 grams per square meter a density of about 0.2 grams per cubic centimeter and comprise 35.4% superabsorbent material. Test samples 12.8 inches wide and 18.2 inches long are cut from the described web. Using an eye dropper an amount equal to approximately 0.2 milliliters of solution A (or B) and C is applied to the test samples in a 1 inch square grid pattern. After application of solutions A (or B) and C a second test sample is placed on top of the first test sample. A large weighted roller (5,448 grams) is rolled back and forth three times over the composite structure. The structure is allowed to equilibrate for 24 hours at room temperature. A number of test samples are so prepared. Additionally, a control sample is prepared by sandwiching two test samples together without applying solutions A, B, or C to said test samples prior to forming the composite structure. The test samples so formed are subjected to various physical property test determinations. The results of the physical property testing and the specific composition of the samples tested are set forth in Table 2.

TABLE 2

| SAMPLE NUMBER | SOLUTIONS | GURLEY STIFFNESS[1] | VERTICAL FIFE[2] | VERTICAL WICKING[3] CAPACITY | ABSORBENT[4] INTEGRITY |
| --- | --- | --- | --- | --- | --- |
| 1* | — | 3.81 | 8.0 | 484 | <5 |
| 2 | A/C | N/D | 8.6 | 500 | >60 |
| 3 | B/C | N/D | N/D | 519 | >60 |

*Not an example of the present invention.
N/D Not determined.
[1]In grams.
[2]Fluid update rate, second insult, in cubic centimeters of liquid per second.
[3]Reported in grams per unit basis weight per unit width.
[4]A 3" × 5" sample is soaked in water and then suspended by one longitudinal end in the air; the time for the sample to break is reported in seconds.

As can be seen from Table 2, the addition of the complex forming materials according to the present invention, does not significantly deteriously affect the absorbent properties of the webs, but significantly improves the integrity of the webs.

Those skilled in the art will recognize that the present invention is capable of many modifications and variations without departing from the scope thereof. Accordingly, the detailed description and examples set forth above are meant to be illustrative only and are not meant to limit in any manner, the scope of the invention as set forth in the following claims.

What is claimed is:

1. A method for improving the integrity of an absorbent fibrous web of material, the steps of the method comprising:
   applying to an absorbent fibrous web of material a first complex-forming material in the form of solid, discrete particles, such that said first complex-forming material is present in said absorbent fibrous web of material;
   applying to an absorbent fibrous web of material, before, after or simultaneously with the first complex-forming material, a second complex-forming material in the form of solid, discrete particles, such that said second complex-forming material is present in said absorbent fibrous web of material;
   wherein at least one of said first or second complex-forming materials is water-soluble; and further
   wherein said first and second complex-forming materials form a complex in the presence of water, which complex formation improves the wet integrity of the absorbent fibrous web.

2. The method according to claim 1 wherein at least one of the first or second complex-forming materials is a polymeric thermoplastic solid having a Vicat softening point between about 30° C. and about 200° C.

3. The method according to claim 2 further comprising the steps of
   (a) heating the absorbent fibrous web above the Vicat softening point of said polymeric thermoplastic solid, after or concurrently with the application of the polymeric thermoplastic solid to the fibrous web; and
   (b) subsequently cooling the web, such that the polymeric thermoplastic solid forms physical bonds between some of the individual fibers of the web.

4. The method according to claim 1, wherein said first and second complex-forming materials are capable of forming a complex in the presence of water by hydrogen bonding, which complex improves the wet integrity of the web.

5. A method for improving the integrity of an absorbent fibrous web of material, the steps of the method comprising:
   applying to an absorbent fibrous web of material a first solid, water-soluble complex-forming material such that said first complex-forming material is present in said absorbent fibrous web of material;
   applying to an absorbent fibrous web of material a second solid, water-soluble complex-forming material, before, after or simultaneously with the first complex-forming material, such that said second complex-forming material is present in said absorbent fibrous web of material;
   wherein at least one of said first or second solid water-soluble complex-forming materials is a thermoplastic polymer and has a Vicat softening point within the range of from about 30° C. and about 200° C., said at least one of said first or second solid water-soluble complex-forming materials binding fibers of the fibrous web together when dry, thereby improving the dry integrity of the web; and
   wherein said first and second complex-forming materials form a complex when wetted, which complex formation improves the wet integrity of the absorbent fibrous web.

6. The method according to claim 5 wherein said first water-soluble complex-forming material is poly (acrylic acid).

7. The method according to claim 6 wherein said second water-soluble complex-forming material is poly (ethylene oxide).

8. The method according to claim 5 wherein said first and second water-soluble complex-forming materials are present in said web in an amount of from about 0.05 to about 5 weight percent based on the total weight of said absorbent web and the ratio of first water-soluble complex-forming material to the second water-soluble complex-forming material is within the range of from about 1:1.5 to about 1.5:1.

9. The method according to claim 5 wherein said second water-soluble complex forming material is poly (ethylene oxide).

10. A method for improving the integrity of an absorbent fibrous web of material, the steps of the method comprising:

applying to an absorbent fibrous web of material a first complex-forming material such that said first complex-forming material is present in said absorbent fibrous web of material;

applying to an absorbent fibrous web of material, before, after or simultaneously with the first complex-forming material, a second complex-forming material such that said second complex-forming material is present in said absorbent fibrous web of material;

wherein at least one of said first or second complex-forming materials is water-soluble; and further wherein said first and second complex-forming materials form a complex in the presence of water, by hydrogen bonding, which complex formation improves the wet integrity of the absorbent fibrous web.

11. The method according to claim 10 wherein said complex-forming material which is water soluble is applied to the absorbent fibrous web in the form of solid, discrete particles.

12. The method according to claim 11 wherein at least one of the first or second complex-forming materials is a polymeric thermoplastic solid having a Vicat softening point between about 30° C. and about 200° C.

13. The method according to claim 12 further comprising the steps of (a) heating the absorbent fibrous web above the Vicat softening point of said thermoplastic solid, after or concurrently with the application of the polymeric thermoplastic solid to the absorbent fibrous web; and (b) subsequently cooling the web, whereby the polymeric thermoplastic solid forms physical bonds between some of the individual fibers of the absorbent fibrous web.

* * * * *